US00PP11482P

United States Patent [19]

Zary

[11] Patent Number: Plant 11,482

[45] Date of Patent: Aug. 15, 2000

[54] HYBRID TEA ROSE PLANT NAMED 'JACSHAQ'

[75] Inventor: Keith W. Zary, Thousand Oaks, Calif.

[73] Assignee: Bear Creek Gardens, Inc., Medford, Oreg.

[21] Appl. No.: 09/215,791

[22] Filed: Dec. 18, 1998

[51] Int. Cl.[7] ..... A01H 5/00

[52] U.S. Cl. ..... Plt./132

[58] Field of Search ..... Plt./130, 132, 137, Plt./138, 139

*Primary Examiner*—Howard J. Locker

*Attorney, Agent, or Firm*—Klarquist Sparkman Campbell Leigh & Whinston, LLP

[57] ABSTRACT

Hybrid tea rose plant having a vigorous, upright growth habit; long stems; large, well-formed flowers; dark green, glossy foliage; and spicy fragrance.

1 Drawing Sheet

The present invention relates to a new and distinct variety of rose plant of the hybrid tea class which was originated by me by crossing the variety 'JACyap' (not patented), with 'TWObe' (U.S. Plant Pat. No. 7901).

The primary objective of this breeding was to produce a new rose variety having a vigorous, upright growing plant; long stems; large, multicolored flowers; dark, glossy foliage; and fragrance. The objective was substantially achieved, along with other desirable improvements, as evidenced by the following unique combination of characteristics that are outstanding in the new variety and that distinguish it from its parents, as well as from all other varieties of which I am aware:

1. Large, well-formed blooms;
2. Color intensity of flowers changes with age;
3. Vigorous, upright, well-branched plant;
4. Dark green, glossy foliage;
5. Long stems; and
6. Spicy fragrance.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'JACyap' (not patented) (unnamed seedling×unnamed seedling).

*Pollen parent.*—'TWObe', U.S. Plant Pat. No. 7901.

Classification:

*Botanical.*—*Rosa hybrida.*

*Commercial.*—Hybrid Tea.

FLOWER

Observations made from specimens grown in a garden environment at Somis, Calif. from January 1996 to October 1998.

Blooming habit: Continuous.

Bud:

*Size.*—1¾ inches long when the petals start to unfurl.

*Form.*—The bud form is long, pointed ovoid.

*Color.*—When sepals first divide, the bud color is Yellow-White Group 158D, with petal edges and tips edged in Red Group 43C. When half blown, the upper sides of the petals are Red Group 43C on the outer ⅓ of the petals. The inner ⅔ are Yellow-White Group 158D and the lower sides of the petals are Yellow-White Group 158D with petal edges being Red Group 43C.

*Sepals.*—Color: Green Group 138C. Surface texture: Covered in many fine hairs. There are three lightly appendaged sepals. There are two unappendaged sepals with hairy edges.

*Receptacle.*—Color: Green Group 137C. Shape: Funnel. Size: Medium (7/16" long×¼" wide). Surface: Smooth.

*Peduncle.*—Length: Short (averaging about 2"). Surface: Glandular. Color: Green Group 137C except when exposed to bright sun. Then it is Greyed-Red Group 178B. Strength: Stiff, erect.

Bloom:

*Size.*—Large. Average open size is 4½ inches.

*Borne.*—Singly.

*Stems.*—Strength: Strong. Average length is 18–22 inches.

*Form.*—When first open: High centered. Permanence: Retains its form to the end. All petals curl back.

*Petalage.*—Number of petals under normal conditions: 30.

*Color.*—The upper sides of the petals are Yellow-White Group 158D with the outer ⅓ of the petal Red Group 43C. The reverse sides of the petals are Yellow-White Group 158D with petal edges being Red Group 43C. The base of the petals has on its upper surface a ¼"×¼" Yellow-Orange Group 15D half moon at the point of attachment. The major color on the upper sides is Yellow-White Group 158D.

*Variegations.*—None.

*Discoloration.*—At the end of the first day: No change. At the end of the third day as the flower opens, the petal surface exposed to sun changes from Yellow-White 158D to Red Group 43C. By day four or five, the Red Group 43C color will intensify to Red Group 43B.

*Fragrance.*—Moderate; spicy.

Petals

*Texture.*—Thick.

*Shape.*—Round.

*Form.*—Tips slightly recurved; edges slightly quilled.

*Arrangement.*—Imbricated. Petaloids in the center: None.

*Persistence.*—Petals drop off cleanly before drying.

*Lastingness.*—On the plant: Long (about seven to eight days). As a cut flower: Long (eight to nine days).

Reproductive parts:

*Anthers.*—Size: Medium. Quantity: Many. Color: Yellow. Arrangement: Regular around styles.

*Filaments.*—Color: Yellow.

*Pollen.*—Color: Gold.

*Styles.*—Color: Reddish.

*Stigmas.*—Color: Greenish-white.

Plant:

*Form.*—Bush.

*Growth.*—Vigorous; upright; branching. At maturity, height is 5 to 5½ feet, and width is 3½".

Foliage: Number of leaflets on normal mid-stem leaves: Five.

*Size.*—Large; 6 inches long×4½ inches wide.

*Quantity.*—Normal.

*Color.*—New foliage: Upper surface: Yellow-Green Group146B in the middle, with Greyed-Purple Group 184A on leaf margins. Lower surfaces: Greyed-Purple Group 184A. Old foliage: Upper Surface: Green Group 139A. Lower Surface: Green Group 138B.

*Shape.*—Oval to pointed oval.

*Texture.*—Upper side: Leathery; glossy.

*Edge.*—Serrated.

*Serration.*—Single; small.

*Petiole rachis.*—Color: Greyed-Purple Group183B.

*Petiole underside.*—Smooth with occasional prickles.

*Stipules.*—Long (¾") serrated; bearded.

*Disease resistance.*—Susceptible to mildew and blackspot, resistant to rust under normal growing conditions.

Wood:

*New wood.*—Color: Greyed-Purple Group 183A. Bark: Smooth.

*Old wood.*—Color: Green Group 137B. Bark: Smooth.

Prickles:

*Quantity.*—On main canes from base: Ordinary. On laterals from main canes: Ordinary.

*Form.*—Medium; hooked downward.

*Color when young.*—Greyed-Purple Group 183A.

*Color when mature.*—Greyed-Red Group 178C.

Small prickles:

*Quantity.*—On main stalks: None. On laterals: None.

I claim:

1. A new and distinct variety of rose plant of the hybrid tea class, substantially as herein shown and described, characterized particularly by its vigorous, upright, well-branched growth habit; long stems; large, well-formed flowers whose color intensity changes with age; dark green, glossy foliage; and spicy fragrance.

* * * * *

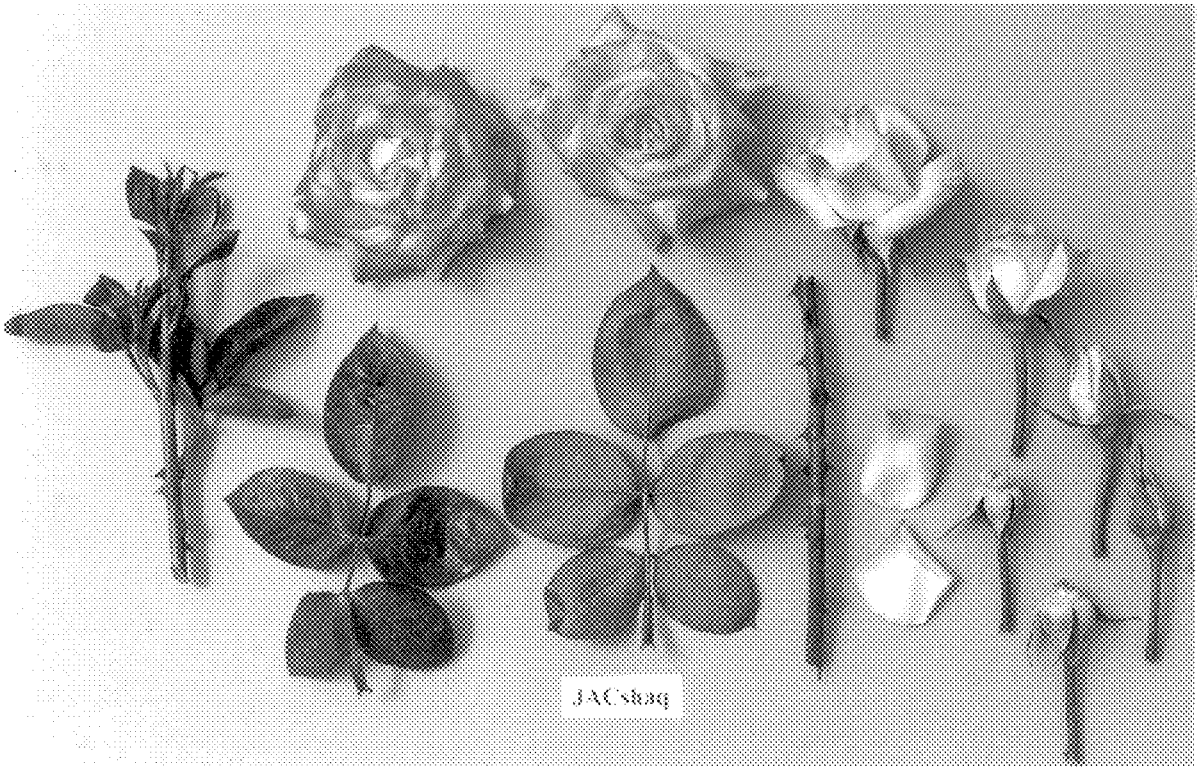
JACSbag

UNITED STATES PATENT AND TRADEMARK OFFICE

CERTIFICATE OF CORRECTION

PATENT NO. : PP 11,482
DATED : August 15, 2000
INVENTOR(S) : Keith W. Zary Ph.D.

It is certified that error appears in the above-identified patent and that said Letters Patent is hereby corrected as shown below:

Column 3,
Line 1, "Petals" should read -- Petals: --.
Line 20, "3½"." should read -- 3½'. --.

Column 4,
Line 7, "(3/4") serrated;" should read -- (3/4"); serrated; --.

Signed and Sealed this

Nineteenth Day of March, 2002

*Attest:*

*Attesting Officer*

JAMES E. ROGAN
*Director of the United States Patent and Trademark Office*